United States Patent [19]

Kendall

[11] 4,350,052

[45] Sep. 21, 1982

[54] APPARATUS AND METHOD FOR TAPPING AND EXTRACTING OIL SAMPLES FROM AN UNDERGROUND HIGH PRESSURE PIPE-TYPE TRANSMISSION CABLE SYSTEM

[75] Inventor: Robert W. Kendall, Seabrook, Md.

[73] Assignee: Elizabeth Virginia Kendall, Wilmington, N.C.

[21] Appl. No.: 173,820

[22] Filed: Jul. 30, 1980

[51] Int. Cl.$^3$ .............................................. G01N 1/10
[52] U.S. Cl. ................................. 73/863.86; 137/318
[58] Field of Search ........... 73/863.81, 863.85, 864.43, 73/864.74; 137/318

[56] References Cited

U.S. PATENT DOCUMENTS

| | | | |
|---|---|---|---|
| 3,229,711 | 1/1966 | Leopold, Jr. et al. | 73/863.85 |
| 3,412,613 | 11/1968 | Brown et al. | 73/864.75 |
| 4,046,013 | 9/1977 | Green | 73/863.85 |

FOREIGN PATENT DOCUMENTS

1216944 12/1959 France .................................. 137/318

Primary Examiner—S. Clement Swisher
Attorney, Agent, or Firm—E. Barron Batchelder

[57] ABSTRACT

Apparatus and method for tapping and extracting an oil sample from a high pressure oil filled pipe-type transmission cable system. The system voltage is very high. Pipe drilling must be carefully controlled to preclude oil and oil pressure release, and to prevent cable conductor contact by the drill. Valve means are attachable to a pipe to be tapped. A fitting having passageway means is attached to the valve. A drill bit extends through the fitting and valve, when in an open position, and is operable to drill a hole through the pipe wall. Sealing means in the fitting are in operative engagement with the drill bit shank and prevent oil and pressure release. Stop means are adjustably positioned on the drill bit shank and are operable to control drilling depth of the drill solely to the pipe wall thickness, and subsequent to drilling to prevent retraction of the drill bit a distance such as to inactivate the sealing means, but to permit valve closure and a subsequent oil sample removal while retaining integrity of the system.

12 Claims, 8 Drawing Figures

APPARATUS AND METHOD FOR TAPPING AND EXTRACTING OIL SAMPLES FROM AN UNDERGROUND HIGH PRESSURE PIPE-TYPE TRANSMISSION CABLE SYSTEM

TECHNICAL FIELD

The present invention relates generally to apparatus and method for tapping and extracting oil samples or removing oil from, or introducing oil into, an electric transmission cable system of the underground high pressure pipe-type. Transmission systems of the type in question involve extremely high voltages, such as 69 kv-230 kv. The pipes which are steel normally enclose a three conductor copper cable, consisting of three copper conductors for three phase systems. The conductors are insulated by oil impregnated paper wrappings, and the three conductors are bound together by means of a brass or aluminum skid wire in spiral wrapped form, to form the completed cable. Such cables are used in insulating oil filled pipes, with the oil being under substantial pressures, such as 300-350 pounds, which increases its insulating value.

Under certain circumstances, it is necessary to tap such cable systems and, in view of the high voltages and high pressure of oil, the tap must be very carefully controlled as regards depth penetration through the pipe to prevent damage to the cable and/or prevent contact with the high voltage conductors. The tap must be made in a manner to preclude loss of oil pressure, and following tapping and taking of an oil sample for testing for contamination therein, the integrity of the cable system must be restored.

At times it is necessary to repair sections of such underground cables because of damage, breakage for various reasons which might include component failure, dislodgement or breakage of the pipe for any reason such as construction work, earthquakes, explosions or the like. When making such repairs, including replacement of sections of the cable system including the pipe and conductors, it is known in the art to freeze sections of the transmission line and then to remove a section thereof and replace the same.

Other circumstances such as suspected deterioration of components which can result in, for example, a build-up and/or accumulation of hydrogen gas in sections of the pipe or in potheads as used in installations, requires tapping and taking of oil samples to run checks for such contaminating materials, etc.

Heretofore, it has frequently been necessary to deactivate portions of a system in order to conduct operations as outlined above. Where major repairs or removal and replacement of sections are required, this of course is necessitated. However, for the purpose of taking samples of the oil in any given pipe location, and/or to determine a freeze condition, for example, permitting removal of a pipe section without a complete loss of or removal of oil and oil pressure, devices have been heretofore substantially unknown.

In the past it has proven difficult to accomplish the tapping of such high pressure, oil filled, underground pipe-type transmission cable systems without a complete shut down of the system, and/or time consuming and highly undesirable removal of oil and/or oil pressure in the system. Time factors in accomplishing tapping and sampling of oil specimens and/or incorporating means for draining such systems and refilling with oil have, while of the essence, not been feasible.

SUMMARY OF THE INVENTION

The present invention accordingly, is broadly directed to the problem of tapping and extracting samples or specimens of oil in high pressure underground pipe-type transmission cable systems as currently in use and in such a manner as to reduce time factors of shut down, prevention of damage to the system and/or personnel and permit such taps and sample extractions to take place in a facile manner.

Accordingly, it is a primary object of the present invention to provide apparatus and a method for tapping and extracting oil samples from a high pressure underground pipe-type electric transmission cable system, utilizing a valve means which can be installed on the pipe casing and the tap and sampling made while normal oil pressures in the pipe are maintained.

A further object of the invention is to provide apparatus whereby the depth of the tap hole can be extremely closely controlled to prevent damage to the conductors therein and permit removal of steel chips through the valve.

An additional object of the invention is to provide such tapping means whereby, subsequent to removal of oil samples, in the absence of loss of oil pressure therein, the overall system can have the integrity thereof restored.

The present apparatus and method is applicable for different line sizes having specifically differing pressure and voltage factors, as also pipe dimensions and the like.

Even more specifically, the invention teaches apparatus for tapping the steel pipe in such systems which includes means to specifically and very carefully control the depth of drill penetration to prevent component and personnel damage and which incorporates means whereby, following or subsequent to the tapping, control means in the nature of a valve can be so activated as to permit removal of an oil sample without a release of the oil pressure in the system.

The apparatus of the invention basically includes a fitting adapted to be attached to a pipe utilized in the underground system of the type involved which can be easily and readily attached, and which can be utilized for many different functions or usages and as effecting the transmission system including, but not limited thereto, the checking for freezes as applied to line sections for removal thereof for repair and/or replacement of sections, evacuation and refilling of such sections, and/or larger extensions of the line, easy tapping at frequent intervals or areas of possible suspect conditions, all without loss of oil pressure in the overall system, damage to the individual conductors or cable and if desired, reuse of the system.

Still other objects and advantages of the present invention will become readily apparent to those skilled in this art from the following detailed description, wherein there is shown and described only a preferred embodiment of the invention, simply by way of illustration of a best mode contemplated currently for carrying out the invention. As will be realized, the invention is capable of other and different specific embodiments and its several details are capable of modification in various, obvious respects, all without departing from the invention. Accordingly, the drawings and description are to be regarded merely as illustrative in nature, and not as restrictive.

BRIEF DESCRIPTION OF DRAWINGS

The accompanying drawings illustrate a preferred embodiment of the invention and, when taken together with the description, serve to explain the principles of the invention.

DETAILED DESCRIPTION OF PREFERRED EMBODIMENT

Figures 1, 2:
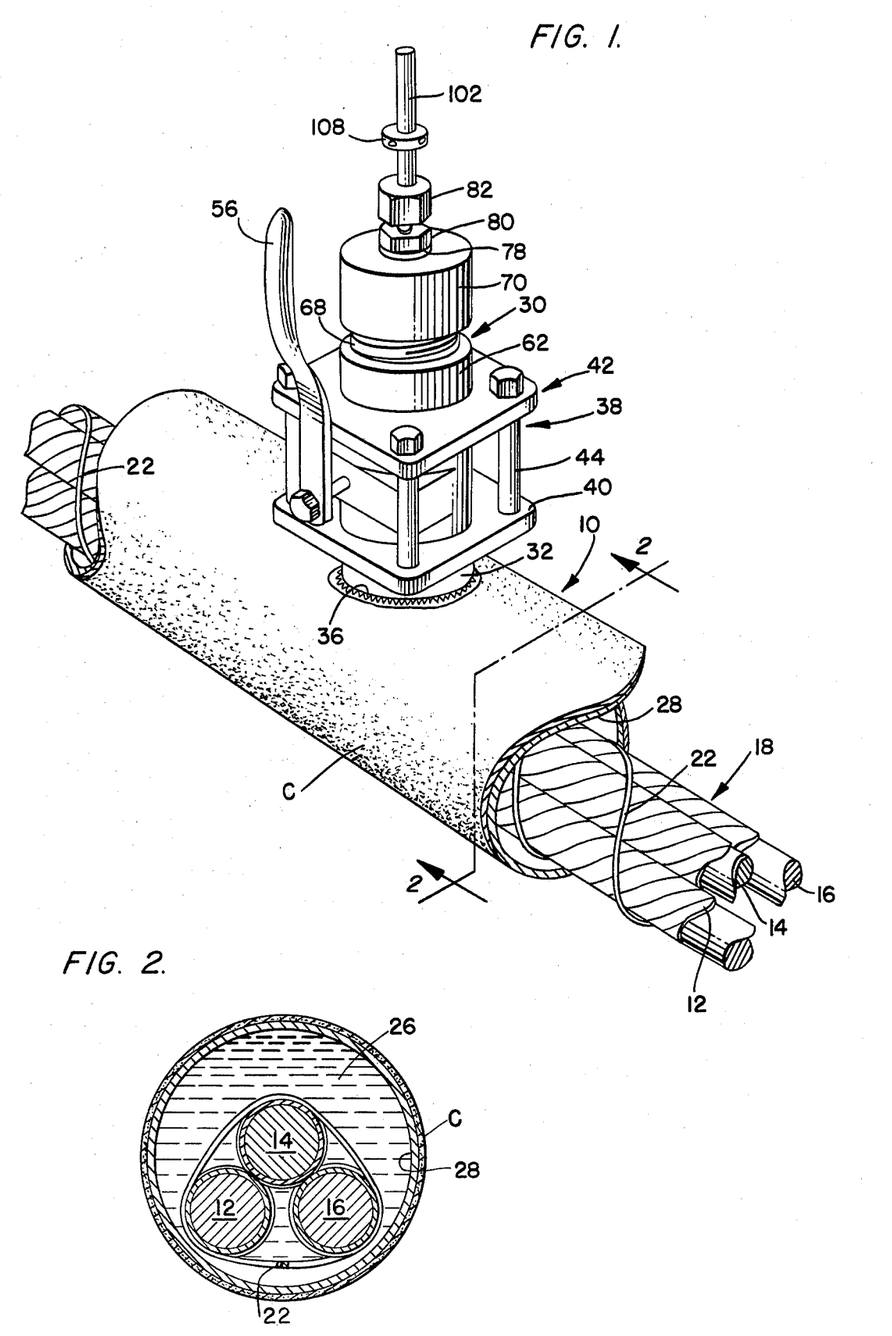
FIG. 1 is a perspective view of apparatus in accordance with the invention as applied to a fragmentarily shown underground oil filled high voltage transmission line system.
FIG. 2 is a sectional view taken on line 2—2 of FIG. 1.

Referring now in detail to the drawings, in FIG. 1, there is disclosed a fragmented section of a high pressure pipe-type transmission cable system of the underground installation type, with the composite line portion being generally designated 10. In such a high voltage, oil filled system, as applied to a three conductor or three phase system, three copper conductors, the individual conductors being designated 12, 14, 16 of an appropriate size, depending upon the voltage of the transmission line, are incorporated and tied together into a composite cable designated 18. In systems of this type, the individual conductors are insulated by means of oil impregnated paper wrappings 20, and so-called skid wires 22 of appropriate material such as brass or aluminum are spirally wrapped therearound. The skid wires are for the purpose of permitting installation of the cable in the pipe and, as used, the skid wire will serve to space the cable from the interior wall of the pipe within which installed to thereby minimize the danger of penetration of the conductor or a cable from the tapping operation. The pipe, subsequent to installation therein of the cable bundle 18 and following the usual line connection in the system, is filled with an insulating oil 26 of a known type. This oil in the system is maintained under pressure and depending upon the exact installation can be in the neighborhood of 300–350 pounds per square inch. In one installation in which the present invention has been utilized, the line voltage is in the range of approximately 138 kv, although in other installations voltages can range from 69 kv to 230 kv. The systems also can utilize different oil pressures depending upon the line size and conditions for which installed.

Also as is known in the art, the specific pipe utilized in the system designated 28 in FIG. 1, for example, is of steel which is weldable material, the individual sections having their ends flared, welded, and bands or chill rings placed within the joints (not shown). The pipes are provided with a pipe lining such as an Epoxy coating, not shown, but known in the art. The exterior surface of the pipe is provided with a coating in a usual and known manner and in one instance the coating is "Somastic" manufactured by Bredero-Price Company and available on the market. This coating C also being known in the art is not specifically shown in detail in the drawings. As will appear hereinafter, however, this external coating on the pipe must be removed prior to installation of the apparatus of the invention.

Installations of the cables in a system such as described provides for the connections of the sections of the pipe as aforementioned and subsequent thereto, with the sections welded to form the overall installed length, a vacuum is placed on or in the pipe to remove all moisture from the line. The cable bundle, consisting of the three conductors as above mentioned and formed, with skid wires, etc. is pulled or drawn through the pipe. A vacuum is again pulled on the system and subsequently the necessary splices or connections are made in manholes, and/or to extend the cable from substation to substation. The pipe is then purged again and the oil is placed in the line and pressurized. Since some installations contemplate a distance of 3000–3500 feet between splices, great care must be taken to ensure the integrity of the system.

The pipes in the system frequently run through or over variations in terrain so that high and low points in the pipe are possible. A circumstance leading to the present invention was an explosion at a pothead. The reason for this explosion was believed to result from hydrogen gas being formed within the pipe of the system and accumulation into a pocket or pockets therein. While the exact reason for formation of a hydrogen gas within the pipe is not completely understood, it is believed that a deterioration of the insulating paper wrapping can occur. It also will be readily understood that such hydrogen gas pockets will form at the high points in a line, which of course are readily determinable, and would be the normal place to tap to check the oil for possible containment of hydrogen therein.

It will also be apparent that as the pipeline is configured, generally speaking, to the terrain over which it extends, the conductor or cable bundle will vary its position within the pipe, i.e., in some instances be closer to the top, the bottom, one or the other side. This is a variable factor, as will be appreciated and must be considered when practicing the invention.

The apparatus or fitting which constitutes the basis or essence of the present invention is shown at 30 as applied to the pipe 28 at a desired selected position. Generally speaking, this fitting includes a nipple 32 which is threaded at its upper end 34 and has its bottom end welded at 36 to the external surface of the pipe, after having removed the coating C from that section of the pipe. A ball valve generally indicated at 38, of a known type usable in high pressure liquid systems, is attached in a fluid tight sealing engagement with the threads of nipple 32. The ball valve as shown in the drawings is of the sectional type, including a lower section 40 and an upper section 42, securable together by nut and bolt combinations 44 cooperating with ears 46 all in a usual manner. As apertured ball 48 is operationally positioned in the usual semicircular recesses 50 in the two valve body sections. The ball valve is preferably of a Teflon lined type, the Teflon lining being shown at 52. A ball operating stem 54 which is attached to the ball extends outwardly of the valve casing in a usual manner, and has an operating handle 56 attached thereto. Each of the sections 40, 42 of the valve body has a bore 58 extending therethrough in a known manner. The aperture 60 or bore extending through the ball in a usual manner is adapted, upon rotation of the ball by handle 56, to mating relationships with the bores 58 to place the ball valve in an open, liquid flow-through condition of the overall valve. As is obvious, a rotation of handle 56 through an angle of 90° will cause a disalignment of ball bore 60 with respect to the bores 58, and liquid flow through the valve is prevented. It is to be noted, as shown for example, in FIGS. 3 and 4, that with the bore 60 aligned with the bores 58a, 58b, there is a through passage extending from opposite ends of the valve body through which, as will appear hereinafter, a drill bit can extend or oil can flow from the pipe after it has been tapped.

An upper nipple 62 is engaged in circular recess 64 at the top of upper valve section 42 and welded therein as shown at 66, thereby creating a fluid-tight seal. The upper end of upper nipple 62 is threaded at 68. An internally threaded cap 70 having a threaded bore 72 extending through the top thereof is operatively engageable on the threaded upper end 68 of the nipple. The cap 70 forms a portion of a fitting or fitment to be selectively mounted or assembled to the valve by intercoaction of the threads of the nipple and cap. A threaded brass fitting 74 having a rectilinear bore or opening 76 therethrough, in screw threadedly engaged in the threaded bore 72 in the preassembly fitting of a fitment generally designated F. A soft copper washer 78 is placed around the brass fitting 74 and superposed on the upper surface of the top of cap 70. A nut shaped intermediate portion 80 on otherwise threaded fitting 74 has a shoulder engaging the washer 78. An internally threaded upper or top cap 82 has an aperture or hole 84 in the top 86 thereof. The cap 82 is, as shown in the drawings, engaged over the upper end of the brass fitting 74, and has a Teflon bushing or washer 88 inserted between the underside of top 86 and the upper end of brass fitting 74. As shown in the exploded, enlarged sectional view of FIG. 4a, the upper end of brass fitting 74 has a conical recess 90 at its upper end extending outwardly from the rectilinear bore 76. The Teflon bushing 88 has a corresponding conical shaped central extension 92, adapted for mating and fluid and pressure sealing engagement in conical recess 92 upon tightening engagement of upper cap 82 on the brass fitting. The Teflon bushing is centrally bored at 94 for mating positionment with the hole 84 of cap 82 and rectilinear bore 76 of the brass fitting 74, in operative positionment of the various portions of the fitting. The top of Teflon bushing 88 has a generally circular flat topped section 96 for operative engagement with the undersurface of the top of cap 82.

Figures 3, 4, 4A:
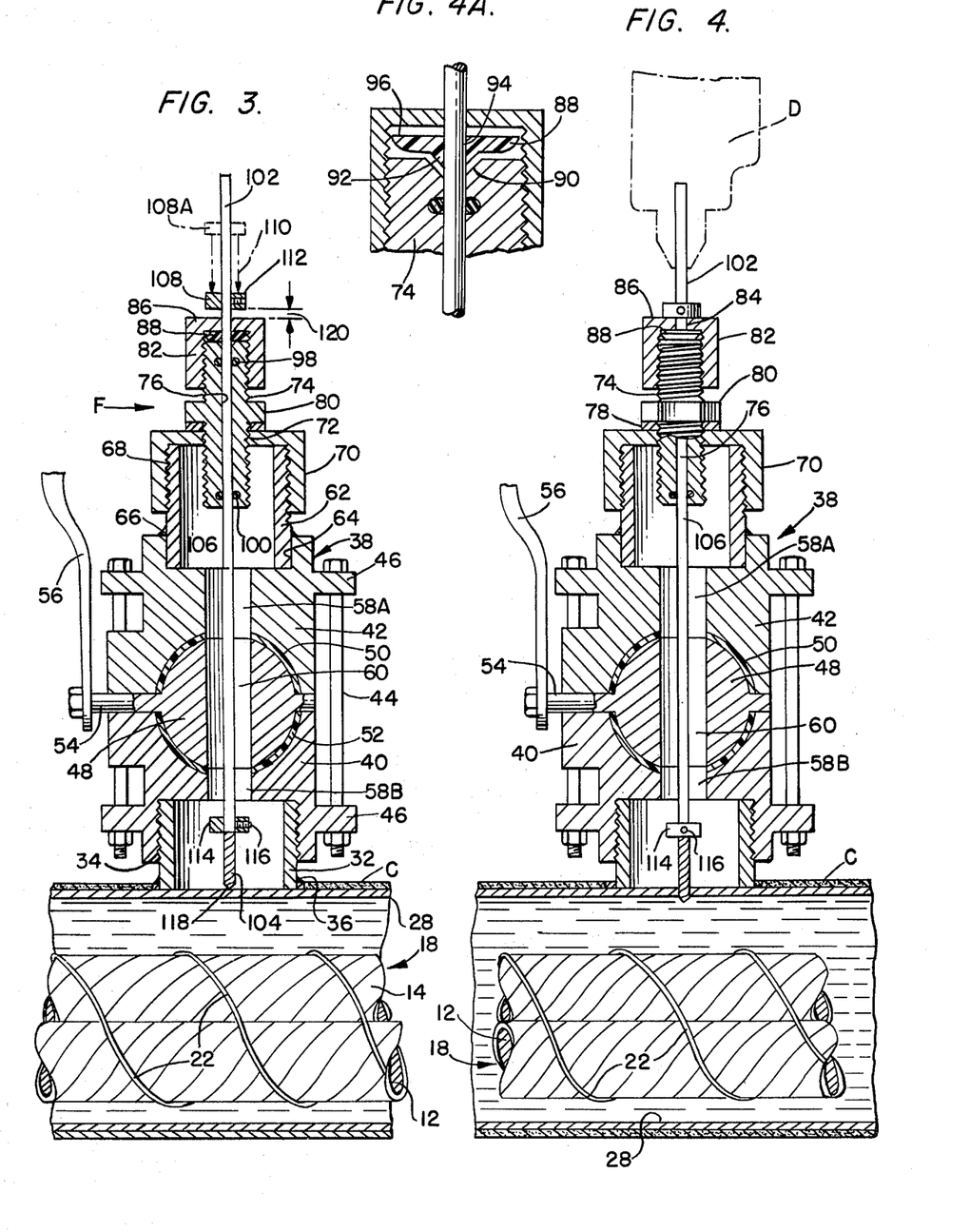
FIG. 3 is a sectional view through the tapping and sampling apparatus of the present invention as applied to the exterior of a pipe prior to the tapping or drilling operation.
FIG. 4 is a view similar to FIG. 3 and disclosing a subsequent operational step of the controlled tapping or drilling through the exterior of the pipe casing to permit access to the oil therein for a desired functional operation thereafter.
FIG. 4A is an enlarged view of a seal bushing.

Upper and lower circular recesses are provided in the rectilinear bore 76 of brass fitting 74 and in which upper and lower O-rings are operatively positioned. A drill bit generally designated 102, of any suitable type, having a fluted drilling end 104 and a lengthy plain shank portion 106 extends through the mating apertures, openings, holes and bores in the fitting F, the lower portion of the drill bit is adapted, upon movement of the ball of the ball valve to the open position as shown in FIGS. 3 and 4, to have the drill end 104 operatively contactable with the wall of pipe 28. The drill can be of any suitable type such as an aircraft drill, and with the shank end and drill flute length being appropriate for drilling through the pipe wall as will be explained hereinafter.

An upper stop nut 108 is slidably positioned on the shank end of the drill bit 102 and is positionally movable as indicated by broken arrows 110 to or from positions 108, shown in solid lines, and 108a in phantom lines. The adjusted position can be fixed by means of set screws 112, preferably having two thereof at 90° angled relationships. A similar lower stop nut 114 is positionally adjustably mounted on the lower end of the drill bit above the fluted section thereof and is slidably adjustable on the non-threaded or plain shank portion for purposes hereinafter to be set forth. Set screws as at 116 are again provided.

When it is desired to tap the pipe wall to permit extraction of an oil sample therefrom while maintaining the pressure on insulating oil within the pipe, the fitting can be preassembled, including cap 70, brass fitting 74, copper washer 78, jam nut 80, O-rings 98, Teflon bushing 88, drill bit 102 extending through the mating openings and bores, and engaging within the internal peripheries of O-rings 98 and the bore in the Teflon bushing 88. The upper stop 108 can be slidably mounted on the upper end of the shank and likewise the lower stop slidably positioned on the lower portion of the drill bit above the threads.

The ball valve upper casing section 42 can have the upper nipple 62 welded in position in circular recess 64 prior to installation of the unit in the field. To this end, since the ball valve casing is preferably Teflon lined, the sections 42 and 40 are separated prior to the welding to prevent damage to the Teflon lining. The fitting together with the ball valve when reassembled, or still in a partially unassembled position, can be taken to the field for ultimate use.

When a position or point of the pipe is considered to be an appropriate position or location, then the nipple 32, which is not associated with the remainder of the apparatus, is welded in position by the weld 36 on the exterior of the pipe 28 subsequent to removal of the coating C therefrom. Due to the pipe sizes normally utilized for transmission lines of the type in question, a pre-configuring of the nipple end to contact the pipe is unnecessary, and as a matter of fact, the weld can overcome any gaps which might exist. Subsequent to positionment and welding of the nipple 32, the lower section of the ball valve can be screw threadedly engaged on the upper threaded end of the nipple. This assembles the ball valve to the nipple in fluid-tight relationship therewith. If desirable, the nipple 32 and ball valve section 40 could be attached by welding, although not believed necessary. The fitting can have been preassembled to the upper nipple, or operatively engaged therewith in the field merely by engagement of the cap 70 on the threaded upper end of upper nipple 62. The drill shank is slidably mounted in the various bores and openings with the outer periphery thereof being in sealing engagement with O-rings 98, 100, and an additional very secure seal being effected by tightening of cap 82 on brass fitting 74 to compress Teflon bushing 88 therebetween in an obvious manner. As mentioned above, oil pressures in the nature of 350 pounds per square inch can be used although, under some circumstances, higher pressures are contemplated in the systems. The O-rings are preferably constructed of Buna N which is oil resistant neoprene, and flexible. The spaced positionment of these O-rings, each of which is designed to withstand 600 pounds per square inch pressure, will accordingly, in conjunction with the Teflon bushing very readily prevent any leakage up to, for example, 1000 pounds per square inch.

Subsequent to assembly of the device on the pipe, the point of the drill bit 118 is brought into engagement with the outer surface of the pipe shell. The wall thickness of the pipe is known. The upper stop 108 is then positioned a distance indicated at 120, between the arrows, above the top surface 86 of cap 82, this relationship being shown in the upper portion of FIG. 3 of the drawings. The upper stop is then secured. The distance 120 is equal to the wall thickness of the pipe and this stop serves to permit the drilling end of the drill to penetrate fully through the wall of the pipe to provide a full hole therethrough but prevent further penetration of the drill into the interior of the pipe. In conjunction with the skid wires around the cable bundle, this limitation of penetration of the drill bit ensures against penetration of the drill into a conductor or through the paper insulation wrapping thereabout. This is a criticality when dealing with high voltage electric transmission cable lines as set forth hereinabove.

Figures 5, 6, 7:
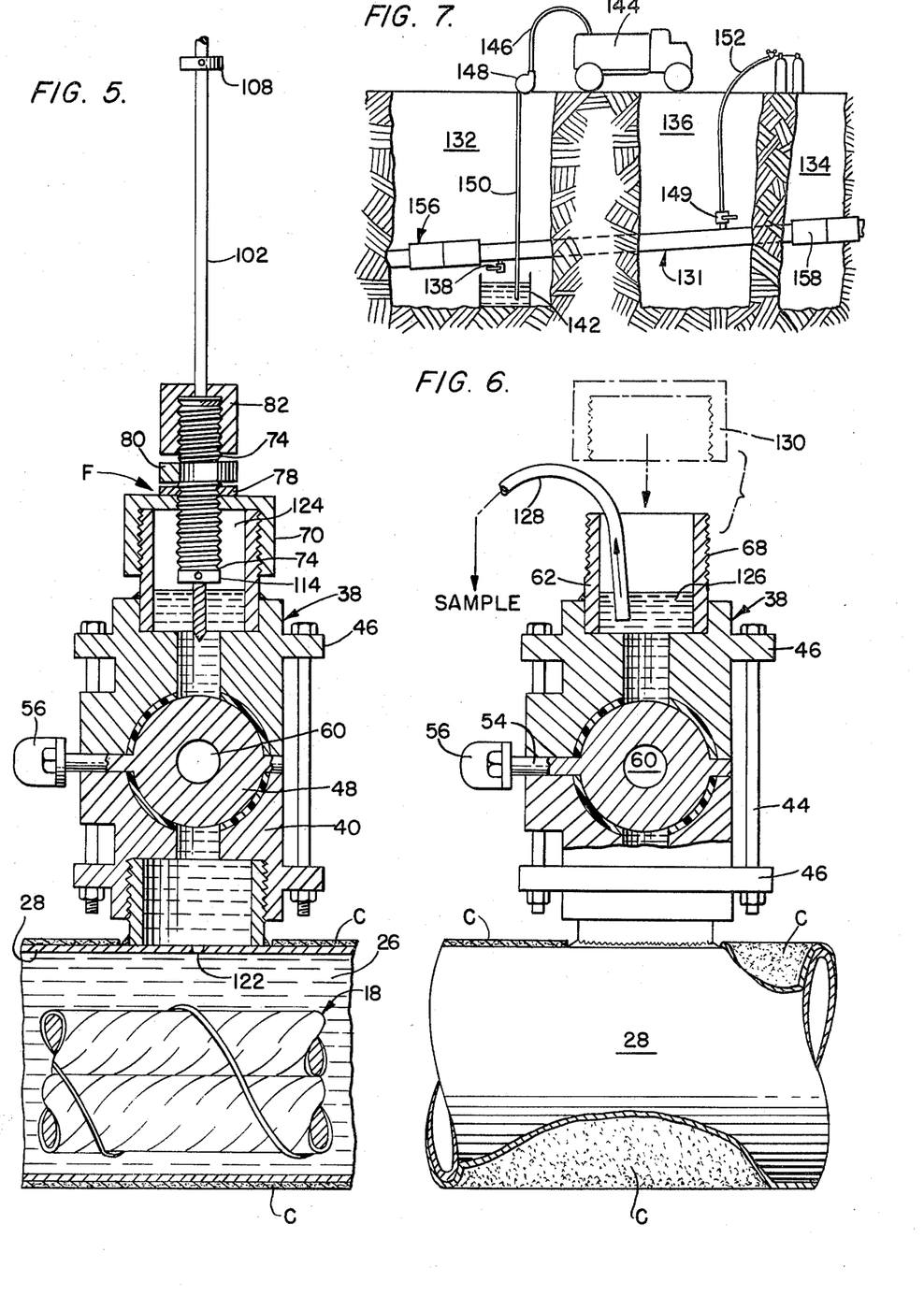
FIG. 5 is a view disclosing the apparatus of FIGS. 3 and 4 in a subsequent step wherein, subsequent to tapping of the pipe, the drill bit is withdrawn, an incorporated valve closed to seal off the oil under pressure in the pipe.
FIG. 6 is a view through the apparatus in a succeeding step wherein an oil sample is removed from the apparatus in the absence of high fluid or oil pressure in the sample taking space, and indicating in phantom lines means for resealing, or sealing of the sample removable chamber for restoration of integrity of the system.
FIG. 7 is a schematic illustration of one possible use of the apparatus of the invention depicting removal of oil from a pipe section subsequent to the freezing of spaced sections thereof.

After the hole shown at 122 in FIG. 5 has been drilled, the drill bit together with drill D, if still connected, is withdrawn from the position shown in FIG. 4 to the position shown in FIG. 5. It is to be noted that lower stop 114 is so positioned on the lower end of the drill bit, in a plain unfluted section thereof that it will, upon withdrawal of the bit, engage with the undersurface of brass fitting 74. This ensures that a seal is maintained between the O-rings, Teflon bushing, etc. to prevent oil under high pressure from flowing outward or out of the fitting. The positionment of lower stop 114 is also so calculated as to permit complete withdrawal of the drill bit fluted end 104 above ball 48 of the ball valve. When so withdrawn following the tapping of the pipe, the ball valve, by means of rotation of handle 56, is turned to the closed position of FIG. 5 wherein the valve ball aperture 60 is out of alignment with the bore 58 of the ball valve housing. It will be seen from FIG. 5 that prior to the closing of the valve, oil has flowed into the lower nipple and mated bores 58, 60 and into the interior of upper nipple 62.

Taking of the sample subsequent to this is very simple. The valve having been closed, the cap 70 is rotated a small amount with respect to its threaded engagement with nipple 62. This slight removal or retraction, through enlargement of the space indicated at 124 in FIG. 5, will remove pressure on the oil. Subsequently, the cap 70 and remainder of fitting F can be removed and a puddle of oil shown at 126, which is under no pressure, permits easy removal in any desired manner. It is readily understandable that containment of the pressurized oil is continued prior to closure of the ball valve by the various seals, and non-withdrawal of the plain shank portion of the drill therefrom.

While a ball valve has been shown, a gate valve or the like could be substituted in a manner understandable to those skilled in the art.

It has been found in actual practice that with the fittings F preassembled or partially preassembled, the set up time in the field for tapping is relatively insignificant. After the nipple is welded in position on the pipe and the rest of the unit assembled, drilling is possible in a period of 15 to 20 minutes, this of course being variable. The older known types in use took a substantially longer period. Prior to the present invention, it sometimes would require a full day to set up for an oil sample taking.

It will be apparent that different sizes of valves can be used depending upon the specific setting or nature of the job to be undertaken. Additionally, the size of the hole to be drilled can vary and the adjustability feature of the stops provides for appropriate use of the apparatus for different wall thicknesses of pipes and under different circumstances of use.

As heretofore pointed out, subsequent to removal or a sample being taken, it is then necessary to restore the integrity of the system, use of the apparatus of the present invention having ensured against loss of oil pressure in the system. It is of course to be understood that there normally are located oil reservoirs at spaced positions along the length of the system lines and pumps are provided to be able to control the pressure of the oil. A lack of oil pressure, or oil in the line, decreases the insulation value. It is additionally known and understood that under operating conditions and high voltage usage, the insulating oil tends to expand. Under this circumstance, the oil will flow to the reservoirs at the spaced positions along the line and is therefore controllable. Pressure variations can accordingly be readily accommodated.

By reference to FIG. 6, the condition for removing the oil sample from oil puddle 126 is schematically illustrated. The sample can be readily removed by a hose such as disclosed at 128 in an obvious manner. The hose 28 is removed and a sealing cap 130 can be engaged onto the upper threaded end 68 of nipple 62 in sealing engagement therewith as schematically indicated. If desired, the cap 130 can be further secued, and the overall system rendered substantially failure and vandal proof by welding of the cap 130 onto the nipple. As is known, the normal capped threads are tapered and in the event reuse of the apparatus is desired, even if the cap has been welded in position, the nipple can be cut or sawed off, with the valve in closed position of course, and another fitting F applied. It is contemplated that the ball valve and upper nipple will remain in the fixed position on the pipe. The initial cost of these parts is relatively insignificant and the set up does permit reuse if desired.

While the foregoing description has been directed primarily to use of the invention for taking of an oil sample, other uses as broadly referred to hereinabove are possible and rendered much easier and less time consuming.

An example of this is depicted in FIG. 7. The pipe of the system is shown at 131. Under some circumstances, failures in the cable line can occur. This might necessitate removal and replacement of a section of the pipe. A known method for accomplishing this removal of a section, in the absence of a complete drainage of the oil from the overall system, incorporates what is known as a freeze method. Access to spaced sections of the underground pipe is made by excavations such as at 132, 134 to expose and make available to workmen the entire exterior of the pipe in these locations which are spacedly positioned at opposite sides of a suspected fault location of the pipe in the excavated area 136. Subsequent to the excavations being effected, the apparatus as disclosed in the preceding figures, and as above described, are connected into the pipe at spaced positions shown at 138 on the bottom of the pipe in excavation 132, and at 140 on the top of the pipe in excavation 136. An oil collection reservoir 142 is placed below the fitting 138, and adapted to collect oil from the pipe upon opening of the apparatus at 138. A tank truck 144 on the ground above the pipe is connected by line 146 through pump 148 to an oil removal pipe 150 which openly extends into reservoir 142. The apparatus 140 is attached by a hose or line 152 to a source of super dry nitrogen indicated at 154, in the usual tanks. At a suspected or actual fault location such as indicated in FIG. 7, where a section of the pipe is to be removed, spaced sections of the pipe have the oil therein frozen by application of refrigerating apparatus generally designated at 156 and 158 in the respective excavations 132, 134. In this known equipment, liquid nitrogen is used which chills and ultimately freezes the oil in the area where the refrigerating apparatus is attached. Such an operation can take 2-3 days. The present invention is very helpful under such circumstances. The apparatus can be attached to the pipe intermediate the refrigerating apparatus and utilized to check the freeze. With the oil frozen at the positions 156, 158, actuation of the fitting F of the apparatus as applied to the pipe will serve initially to release pressure in the line and, if the freeze is complete, no flow of oil subsequent to such release will occur. If desired, a pressure gauge could be incorporated in the fitting for a visual reading of the pressure conditions. The present invention is accordingly helpful to check as to whether or not a freeze has been made. Subsequent thereto, the fitting can be used to remove oil still in the pipe between the freeze points, such as depicted in FIG. 7, by opening the fitment 138 to drain oil into the reservoir and then to pump the same into the tank truck for removal, utilizing the super dry nitrogen to facilitate oil removal. As will be obvious, the reverse of the situation shown in FIG. 7 is possible, i.e., subsequent to replacement of a cable section, by a reverse operation of purging of the line, oil can be placed within the replaced section and pressurized so that the integrity of the system is ensured.

Another apparent use of the apparatus of the present invention is to bleed off air pockets in oil transmission lines, for example. In other high pressure transmission systems, the present invention could be utilized for removal of samples of fluid, to remove vapor locks, and/or check for contamination in the fluid, etc. It will accordingly be seen that the present invention permits numerous uses of means for tapping pipes or lines containing fluids under high pressure, while maintaining the overall integrity of the system, and permitting restoration of the system subsequent to the sample removal. Repairs and/or connections can be effected in such pipeline systems by use of the facile apparatus of the invention.

Many other uses and possible variations in components or details of the invention will be apparent to those skilled in the art. While in the present disclosure, there is shown and described a preferred embodiment of the invention, it is to be understood that the invention is capable of changes or modifications without departing from the spirit and the scope of the inventive concept as expressed herein.

I claim:

1. Apparatus for tapping and extracting an oil sample from a high pressure pipe-type transmission cable system comprising valve means operatively attached to the exterior of said pipe, said valve means being operable to open and closed positions to permit access therethrough to said pipe, a fitting operatively attached to said valve means remote from said pipe, said fitting having a bore therethrough in communication with said valve, a drill bit slidably and rotatably extending through said bore and said valve means when in an open position, with a work end thereof being engageable with said pipe, and the remote end being adapted for connection to a drill driving means, resilient fluid sealing means operatively mounted in said bore in said fitting, a fluid sealing bushed packing nut in operative adjustable engagement on the free end of said fitting, said drill bit extending through said fluid sealing means and said bushed packing nut, stop means on said drill bit external of said fitting, said stop means being adjustable on said drill bit to limit depth of a tap hole drilled in said pipe to the wall thickness thereof, said sealing means and said bushed packing nut being operative to permit drilling of the tap hole while maintaining normal oil pressure in said system, partial withdrawal of said drill bit subsequent to drilling the tap hole permitting oil flow into said fitting and a subsequent closure of said valve means sealing off pressurized oil flow from said pipe, said fitting including an adjustable cap movable toward and away from the fitted end and operable, upon adjustment away from the fitting end, to increase the interior volume of said fitting and thereby relieve pressure of oil contained in the fitting and permitting a subsequent opening of the fitting to permit access to pressure relieved and therefore non-pressurized oil contained therein.

2. Apparatus as defined in claim 1, including second stop means adjustably mounted on said drill bit intermediate said work end and said drill connection end, on a plain shank portion of said drill bit, internally of said fitting and adapted to limit the said partial withdrawal of said drill bit to a position such that the plain shank portion is maintained in oil sealing engagement with said O-ring means, and said bushed packing nut, with the drill bit removed a distance beyond said valve means to permit closing thereof to seal off oil under pressure in said pipe from the interior of said fitting.

3. Apparatus for tapping and extracting an oil sample from an underground high pressure oil filled pipe-type electric transmission cable comprising a first pipe nipple adapted for engagement with and welding to the exterior of a said pipe, a ball valve including a casing having a first end attached to the free end of said first pipe nipple and having a flow bore therein, a Teflon ball valve seat insert in said ball valve casing, said insert having openings mating with said flow bore, a valve ball rotatably mounted in said seat insert, said valve ball having a flow passage therethrough, means exterior of said ball valve casing to rotate said valve ball in said seat insert to valve open and closed positions, respectively, to selectively align and disalign said flow passage in said valve ball with respect to said flow bore in said casing to thereby selectively permit and prevent oil flow through said ball valve, a second nipple attached to a second said casing end opposite said first end, said second nipple having a threaded free end, an internally threaded closure cap engaged on said second nipple threaded free end, said closure cap having an end face, a threaded bore extending through said end face, a pipe tapping fitting installed in said closure cap, said pipe tapping fitting including a cylindrical sleeve having externally threaded ends and an intermediate shoulder means of larger diameter than said threaded ends and having flat longitudinal ends, said cylindrical sleeve having a smooth internal bore extending therethrough, one said threaded end of said sleeve being threadedly engaged in said threaded bore in said closure cap and extending into the interior of said closure cap, the other of said threaded ends of said sleeve extending outwardly from said end face of said closure cap, a flat-faced sealing washer mounted on said sleeve with one said face in engagement with the end face of said closure cap, said shoulder means of said sleeve having one said flat longitudinal end engaged with the other of said flat faces of said sealing washer, said cylindrical sleeve and said threaded bore being so threadedly interengaged as to compress said sealing washer between the contacting face of said shoulder means and end face of said closed closure cap and forming a fluid tight seal therebetween, a drill bit inserted through said smooth internal bore of said cylindrical sleeve, said drill bit having a fluted drilling end and a smooth shank portion, longitudinally spaced O-rings mounted in said smooth internal bore of said cylindrical sleeve, said smooth shank portion of said drill bit being slidably and rotatably positioned in said smooth internal bore and in pressure and fluid tight sealing engagement with said O-rings, a compressible and resilient Teflon bushing member movably positioned on said smooth shank portion of said drill bit, an internally threaded cup shaped packing nut having an end opening slidably engaged on said smooth shank portion of said drill bit, said packing nut being adjustably threadedly engaged on said other of said threaded ends of said cylindrical sleeve extending outwardly from said end face of said closure cap and engaging said Teflon bushing member for applying pressure and fluid tight sealing engagement around and between said drill bit shank and said internal bore of said sleeve upon tightening adjustment of said packing nut to compress said Teflon bushing, with said drill bit being operatively rotatable therein, said drilling end of said drill bit being engageable with said pipe and adapted upon rotation to drill a hole through the wall of said pipe, stop means on said drill bit shank, said stop means being positionally adjustable on said drill bit shank to engage the free end of said packing nut to limit drill bit travel and depth of drilling penetration to specifically the wall thickness of said pipe, and thereby prevent penetration of said drill bit into the interior of said pipe, and into inadvertent contact with an electric cable therein.

4. Apparatus as claimed in claim 3, including second stop means adjustably mounted on said drill bit intermediate said drilling end and said plain shank portion of said drill bit, disposed internally of said closure cap and adapted to limit withdrawal of said drill bit, by contact with the inner side of said end face thereof, to a position such that the smooth shank portion is maintained in oil sealing engagement with said O-rings, and said Teflon bushing member, with the drill bit removed a distance beyond said valve ball to permit closing thereof to seal off oil under pressure in said pipe from the interior of said fitting.

5. Apparatus for tapping and extracting an oil sample from a high pressure pipe-type transmission cable system comprising valve means operatively attached to the exterior of said pipe, said valve means being operable to open and closed positions to permit access therethrough to said pipe, a fitting operatively attached to said valve means remote from said pipe, said fitting having a bore therethrough in communication with said valve, a drill bit slidably and rotatably extending through said bore and said valve means when in an open position, with a work end thereof being engageable with said pipe, and the remote end being adapted for connection to a drill driving means, resilient fluid sealing O-ring means operatively mounted in said bore in said fitting, a fluid sealing bushed packing nut in operative adjustable engagement on the free end of said fitting, said drill bit extending through said O-ring means and said bushed packing nut, stop means on said drill bit external of said fitting, said stop means being adjustable on said drill bit to limit depth of a tap hole drilled in said pipe to the wall thickness thereof, said O-ring means and said bushed packing nut being operative to permit drilling of the tap hole while maintaining normal oil pressure in said system, partial withdrawal of said drill bit subsequent to drilling the tap hole permitting oil flow into said fitting and subsequent closure of said valve means to seal off pressurized oil flow from said pipe, said fitting being adjustable to relieve pressure of oil contained therein and subsequent opening to permit access to non-pressurized oil contained therein and including second stop means adjustably mounted on said drill bit intermediate said work end and said drill connection end, on a plain shank portion of said drill bit, internally of said fitting and adapted to limit the said partial withdrawal of said drill bit to a position such that the plain shank portion is maintained in oil sealing engagement with said O-ring means, and said bushed packing nut, with the drill bit removed a distance beyond said valve means to permit closing thereof to seal off oil under pressure in said pipe from the interior of said fitting, said fitting including a cylindrical sleeve having said bore therethrough, the opposite external end portion of said sleeve being threaded, an intermediate external portion of said sleeve being non-threaded, said packing nut being threadedly engaged on a first free threaded end portion of said sleeve, a threaded end nipple attached to said valve means remote from said pipe, a cup-shaped closure cap threadedly engaged on said threaded nipple end, and having a threaded end portion operatively engaged in and extending through said threaded end hole to the interior of said closure cap, said closure cap being adjustable on said nipple to increase the interior volume within said nipple and said closure cap and thereby relieve pressure of oil contained in said fitting.

6. Apparatus as claimed in claim 5, including a soft copper washer mounted on said sleeve and interfaced between said intermediate non-threaded external sleeve portion and the outer face surface of said closure cap, tightening adjustment of said closure cap sealingly interengaging said washer between said sleeve and face of said closure cap.

7. Apparatus as claimed in claim 6, said bushed packing nut comprising an internally threaded cup-shaped cap having an end bore therethrough, said drill bit having a plain shank end extending through said end bore and adapted for operative attachment to bit driving means, a Teflon sealing washer on said drill bit shank intermediate the under face surface of said cup-shaped cap and the free end of said sleeve, said cup being adjustable to functionally compress and sealingly engage said Teflon washer to said free end of said sleeve and about the external surface of said drill bit shank to additively increase pressure sealing within said fitting and about said drill bit shank.

8. Apparatus as claimed in claim 7, said stop means external of said fitting comprising an adjustable positioned stop nut mounted on said drill bit shank externally of said cup-shaped packing nut cap, depth of tap hole drilling being controllable by initially engaging the drill bit end with the pipe exterior and spacedly fixedly positioning said stop nut from the outer face surface of said packing nut cap a distance equal to the known wall thickness of the pipe, contact between said stop nut and said packing nut cap limiting linear movement of said drill bit and thereby depth of drilling.

9. Apparatus as claimed in claim 1, wherein the valve attachment means comprise a nipple welded to the exterior of the pipe at a location to be tapped, the free end of said nipple being externally threaded, said valve means being screw threadedly engaged to said nipple free end.

10. A method of tapping and extracting an oil sample from apparatus such as a high pressure pipe-type transmission cable system and the like comprising operatively attaching selectively operable valve means to the exterior of said apparatus, operatively attaching a bored fitting to the valve means remote from the apparatus, with the bore positioned for communication with the valve in an open position, slidably and rotatably extending a drill bit through the bore and valve means when in an open position and maintaining a fluid and pressure seal in the bore with the drill bit, engaging the work end of the drill bit with the apparatus, fixing stop means on the drill bit externally of the fitting with the stop means being spaced from the fitting a distance equal to the wall thickness of the apparatus to limit depth of a tap hole drilled to the wall thickness thereof, maintaining the seal subsequent to drilling while retracting the drill bit to a location permitting closure of the valve means, and while maintaining normal oil pressure in said system, partially withdrawing the drill bit subsequent to drilling the tap hole and permitting oil flow into the fitting, subsequently closing the valve means and thereby sealing off pressurized oil flow from said apparatus, and thereafter adjusting the fitting to reduce pressure of oil contained therein to substantially atmospheric pressure, and subsequently opening the fitting for access to and removal of the non-pressurized oil contained therein.

11. Apparatus for tapping and permitting extracting an oil sample at substantially atmospheric pressure from a container normally having oil under very high pressure therein, comprising: valve means having a bore therethrough, and attachable to said container, said valve being movably mounted to selectively dispose the bore in open and closed positions, a fitting connected to said valve means, said fitting having a passageway therethrough operatively mateable with said valve bore in open position, means forming an oil reservoir above the fitting passageway, a rotatable drill bit adjustably extendable and retractable through said passageway and valve bore in an open and mated position thereof, said drill bit having a drilling end, operable upon drill extension and rotation, to drill a tap hole solely through the thickness of the container wall into the interior thereof, fluid sealing means operable to prevent oil under pressure from flowing between said drill bit and said passageway in extended and retracted positions of said drill bit and subsequent to drilling of a said tap hole, multiple adjustable linear movement stop means on said drill bit, said stop means being adjustable to limit linear extension and retraction of said drill bit, and an adjustable bored top cap on the free end of said fitting in selective sealing engagement therewith, said drill bit having a driveable end extended through said bored top cap, said cap being adjustable, subsequent to tapping of said container and closure of said valve, to increase the size of said reservoir and thereby reduce pressure of the oil to substantial atmospheric pressure for subsequent removal from the apparatus reservoir for quality testing for the presence of gases or other material therein which would serve to indicate a possible deterioration or breakdown of operating means within the container.

12. A method of tapping and extracting an oil sample from apparatus as claimed in claim 10, said apparatus comprising a high pressure pipe-type transmission cable system.

* * * * *